(12) United States Patent
Allegretti et al.

(10) Patent No.: US 8,624,036 B2
(45) Date of Patent: Jan. 7, 2014

(54) 2-ARYL-PROPIONIC ACIDS AND DERIVATIVES AND PHARMACEUTICAL COMPOSITIONS CONTAINING THEM

(75) Inventors: Marcello Allegretti, L'Aquila (IT); Andrea Aramini, L'Aquila (IT); Gianluca Bianchini, L'Aquila (IT); Maria Candida Cesta, L'Aquila (IT)

(73) Assignee: Dompe S.p.A., L'Aquila AQ (IT)

( * ) Notice: Subject to any disclaimer, the term of this patent is extended or adjusted under 35 U.S.C. 154(b) by 0 days.

(21) Appl. No.: 13/063,105

(22) PCT Filed: Sep. 18, 2009

(86) PCT No.: PCT/EP2009/062109
§ 371 (c)(1),
(2), (4) Date: May 5, 2011

(87) PCT Pub. No.: WO2010/031835
PCT Pub. Date: Mar. 25, 2010

(65) Prior Publication Data
US 2011/0207785 A1    Aug. 25, 2011

(30) Foreign Application Priority Data

Sep. 18, 2008   (EP) ................................... 08164605

(51) Int. Cl.
  *A61K 31/421*  (2006.01)
  *A61K 31/426*  (2006.01)
  *C07D 263/48*  (2006.01)
  *C07D 277/42*  (2006.01)
(52) U.S. Cl.
  USPC ............ 548/190; 548/234; 514/370; 514/377
(58) Field of Classification Search
  USPC ................................................. 548/190, 234
  See application file for complete search history.

(56) References Cited

U.S. PATENT DOCUMENTS 4,025,528 A   5/1977 Maeda et al.

FOREIGN PATENT DOCUMENTS

| EP | 0935961    | 8/1999 |
| EP | 1 123 276  | 1/2003 |
| GB | 1 481 465  | 7/1977 |
| WO | WO00/24710 | 5/2000 |
| WO | WO 01/58852| 8/2001 |
| WO | WO 03/043625| 5/2003 |

OTHER PUBLICATIONS

Sawhney et al., Indian Journal of Chemistry, Section B: Organic Chemistry Including Medicinal Chemistry (Jul. 1978), 16B(7), pp. 605-609.*
Patani et at, "Bioisosterism: A Rational Approach in Drug Design," Chemical Reviews, 96(8), pp. 3147-3176, Jan. 1, 1996.
Wermuth et al., "Molecular Variations Based on Isosteric Replacements," Practice of Medicinal Chemistry, pp. 203-237, Jan. 1, 1996.
Abe, Y., et al., Transient rise in serum interleukin-8 concentration during acute myocardial infarction, Br. Heart J. 1993, 70: 132-134.
Akgun, H., et al., Synthesis of some 2-Arylpropionic acids amides as prodrugs, Arzeim-Forg./Drug Res. 1996, 46: 891-894.
Bizzarri, C., et al., Selective inhibition of interleukin-8-induced neutrophil chemotaxis by ketoprofen isomers, Biochem. Pharma. 2001, 61: 1429-1437.
Carre, P., et al., Increased Expression of the Interleukin-8 Gene by Alveolar Macrophages in Idiopathic Pulmonary Fibrosis, J. Clin. Invest. 1991, 88: 1802-1810.
Chang, Q., et al., The melanoma growth stimulatory activity receptor consists of two proteins, J. Immunol. 1992, 148: 451-456.
Dirnagl,. U., et al., Pathobiology of ischaemic stroke: an integrated view, Trends Neurosci. 1999, 22: 391-397.
Falk, W., et al,. A 48-well micro chemotaxis assembly for rapid and accurate measurement of leukocyte migration, J. Immuno. Methods 1980, 33: 239-247.
Ghezzi, P., et al, Differential Contribution of R and S Isomers in Ketoprofen Anti-inflammatory Activity: Role of Cytokine Modulation, J. Pharma. & Exp. Therapeutics 1998, 287: 969-974.
Gougerot-Podicalo, MA et al., Modulation de l'explosion oxidative des polynucleaires neutrophils humains par les cytokines pro-et anti-inflammatoires, Path Biol. 1996, 44: 36-41 (with English abstract).
Haringman, JJ et al., Chemokines in joint disease: the key to inflammation? Ann Rheum Dis 2004, 63: 1186-1194.
Jiang, N., et al., Neutrophil inhibitory factor treatment for focal cerebral ischemia in the rat, Brain Research 1998, 25-34.
Katschke, K., et al., Differential Expression of Chemokine Receptors on Peripheral Blood, Synovial Fluid, and Synovial Tissue Monocytes/Macrophages in Rheumatoid Arthritis, Arthritis & Rheumatism 2001, 44: 1022-1032.
Koch, A., et al., Synovial tissue macrophage as a source of the chemotactic cytokine IL-8, J. Immunol. 1991, 147: 2187-2195.
Liu, Z., et al., The role of complement in experimental bullous pemphigoid, J. Clinical Invest. 1995, 95: 1539-1544.
Matsumoto, T., et al., Prevention of cerebral edema and infarct in cerebral reperfusion injury by an antibody to interleukin-8, Laboratory Investigation 1997, 77: 119-122.
Mazzaone, A., et al., Ruolo dei granulociti nella cardiopatia ischemia, Recenti Progessi in Medicina 1994, 85: 397-406 (with English abstract).
Ming, W., et al., Tumor necrosis factor is chemotactic for monocytes and polymorphonuclear leukocytes, J. Immunol. 1987, 138: 1469-1474.
Patrignani, P., et al., Biochemical and pharmacological characterization of the cyclooxygenase activity of human blood prostaglandin endoperoxide synthases, J. Pharma & Exp. Therapeutics 1994, 271: 1705-1712.

(Continued)

*Primary Examiner* — Laura L. Stockton
(74) *Attorney, Agent, or Firm* — Steinfl & Bruno LLP

(57) ABSTRACT

The present invention relates to (R,S) 2-aryl-propionic acids and derivatives, their single enantiomer (S) and to pharmaceutical compositions containing them, which are used in the prevention and treatment of tissue damage due to the exacerbated recruitment of polymorphonucleated neutrophils (PIvTN leukocytes) at inflammation sites. The present invention provides compounds for use in the treatment of transient cerebral ischemia, bullous pemphigo, rheumatoid arthritis, idiopathic fibrosis, glomerulonephritis and damages caused by ischemia and reperfusion.

12 Claims, No Drawings

(56) References Cited

OTHER PUBLICATIONS

PCT International Preliminary Report on Patentability issued on Mar. 22, 2011 for PCT Application PCT/EP2009/062109 filed on Sep. 18, 2009 in the name of Dompe S.P.A.

PCT International Search Report mailed on Apr. 28, 2010 for PCT Application PCT/EP2009/062109 filed on Sep. 18, 2009 in the name of Dompe S.P.A.

PCT Written Opinion mailed on Apr. 28, 2010 for PCT Application PCT/EP2009/062109 filed on Sep. 18, 2009 in the name of Dompe S.P.A.

Podolin, P., et al., A Potent and Selective Nonpeptide Antagonist of CXCR2 Inhibits Acute and Chronic Models of Arthritis in the Rabbit, J. immunol. 2002, 6435-6444.

Ransohoff, R., et al., Do chemokines mediate leukocyte recruitment in post-traumatic CNS inflammation?, TINS 1998, 21: 154-159.

Remington's Pharmaceutical Sciences Handbook, 18th Edition, 1990, pp. 1434-1705 (8 parts).

Ricevuti, G., et al., Role of granulocytes in endothelial injury in coronary heart disease in humans, Athero. 1991, 91: 1-14.

Schmidt, E., et al., Autoantibodies to BP180 associated with bullous pemphigold release interleukin-8 from cultured human keratinocytes, Soc. for Invest. Dermatology 2000, 115: 842-848.

Seitz, M., et al., Enhanced production of neutrophil-activating peptide-1/interleukin-8 in rheumatoid arthritis, J. Clin. Invest. 1991, 87: 463-469.

Sekido, N., et al., Prevention of lung reperfusion injury in rabbits by a monoclonal antibody against interleukin-8, Nature 1993, 365: 654-657.

Szekanecz, Z., et al., Cellular adhesion molecules in rheumatoid arthritis: Regulation by cytokines and possible clinical importance, J. Invest. Med. 1996, 44: 124-131.

Szekanecz, Z., et al., Chemokines and chemokine receptors in rheumatoid arthritis, Seminars in Immunol. 2003, 15: 15-21.

Van Damme, J., et al., Identification by sequence analysis of chemotactic factors for monocytes produced by normal and transformed cells stimulated with virus, double-stranded RNA or cytokine, Eur. J. Immunol. 1989, 19: 2367-2373.

Wada, T., et al., Prevention of proteinuria by the administration of anti-interleukin 8 antibody in experimental acute immune complex-induced glomerulonephritis, J. Exp. Med. 1994, 180: 1135-1140.

Witko-Sarsat, V., et al., Neutrophils: Molecules, Functions and Pathophysiological Aspects, Lab. Invest. 2000, 80: 617-652.

Xu, L., et al., Modulation of IL-8 receptor expression on purified human T lymphocytes is associated with changed chemotactic responses to IL-8, J. Leukocyte Biol. 1995, 57: 335-342.

Yamagami, S., et al., Differential production of MCP-1 and cytokine-induced neutrophil chemoattractant in the ischemic brain after transient focal ischemia in rats, J. Leukocyte Biol. 1999, 65: 744-749.

Yamasaki, Y., et al., Transient increase of cytokine-induced neutrophil chemoattractant, a member of the interleukin-8 family, in ischemic brain areas after focal ischemia in rats, Stroke 1995, 26: 318-325.

Yamasaki, Y., et al., New therapeutic possibility of blocking cytokine-induced neutrophil chemoattractant on transient ischemic brain damage in rats, Brain Research 1997, 759: 103-111.

* cited by examiner

2-ARYL-PROPIONIC ACIDS AND DERIVATIVES AND PHARMACEUTICAL COMPOSITIONS CONTAINING THEM

BRIEF DESCRIPTION OF THE INVENTION

The present invention relates to (R,S) 2-aryl-propionic acids and derivatives, their single enantiomer (S) and to pharmaceutical compositions containing them, which are used in the prevention and treatment of tissue damage due to the exacerbated recruitment of polymorphonucleated neutrophils (PMN leukocytes) at inflammation sites.

STATE OF THE ART

Particular blood cells (macrophages, granulocytes, neutrophils, polymorphonucleated) respond to a chemical stimulus by migrating along the concentration gradient of the stimulating agent, through a process called chemotaxis. Chemokines constitute a large family of chemotactic cytokines that exert their action via an interaction with receptors belonging to the 7TM-GPCRs family. The chemokine system is crucial for the regulation and the control of the basal homeostatic and inflammatory leukocyte movement. The functional consequences of chemokine receptor activation include leukocyte locomotion, degranulation, gene transcription, mitogenic and apoptotic effects.

Other chemotactic factors not belonging to the GPCRs family are known, including the breakdown products of complement C5a, some N-formyl peptides generated from lysis of the bacterial surface or peptides of synthetic origin, such as formyl-methionyl-leucyl-phenylalanine (f-MLP) and mainly by a variety of cytokines, including interleukin-8 (CXCL8).

CXCL8 (interleukin-8) is an endogenous chemotactic factor produced by most nucleated cells such as fibroblasts, macrophages, endothelial and epithelial cells. Belonging to the family of this chemotactic factor is a series of CXCL8-like chemokines [GRO α, β, γ and NAP-2], which bind to the CXCL8 receptors CXCR1 and CXCR2 (Chang et al., J. Immunol., 148, 451, 1992). Neutrophils are the first line of defense against bacterial infection, owing to the ability of these cells to migrate from the peripheral blood through the endothelial junctions and the tissue matrices towards the action sites (i.e. along chemotactic factor concentration gradients) where they act by attacking the microorganisms, removing damaged cells and repairing tissues (M. A. Goucerot-Podicalo et al., Pathol. Biol (Paris), 44, 36, 1996).

In some pathological conditions, marked by exacerbated recruitment of neutrophils, a more severe tissue damage at the site is associated with the infiltration of neutrophils. The role of neutrophilic activation in the determination of damage associated with post-ischemia reperfusion and pulmonary hyperoxia was widely demonstrated. Experimental models [N. Sekido et al., Nature, 365, 654, 1993 and T. Matsumoto et al., Lab. Investig., 77, 119, 1997] and clinical studies (A Mazzone et al., Recent Prog. Med., 85, 397, 1994; G. Receipts et al., Atheroscl., 91, 1, 1991) have shown the direct correlation between cellular damage and the extent of PMN leukocyte infiltration, CXCL8 being the most specific and powerful activator thereof.

The specific role of CXCL8 in causing damage following post ischemia reperfusion in patients affected by acute myocardium infarction was shown (Y. Abe et al., Br. Heart J., 70, 132, 1993). Experimental studies have shown recruitment and influx into the lesioned brain of vascular leukocytes, mainly PMNs, in the early post-ischemic period and, later, monocytes/macrophages, expression of proinflammatory cytokines, chemokines and adhesion molecules (U. Dirnagl et al., Trends Neurosci., 22, 391, 1999). Activated PMNs contribute to brain injury by causing microvascular occlusion and production of toxic mediators, like cytokines, reactive oxygen and nitrogen metabolites and lipid mediators (V. Witko-Sarsat et al., Lab. Invest., 80, 617, 2000). The role of PMN infiltration in the development of ischemia-induced damage and strategies to reduce PMN accumulation have been studied in transient cerebral ischemia animal models (N. Jiang et al., Brain Res., 788, 25, 1998). It has been hypothesized that PMN chemoattractant CXC chemokines, including CXCL8, are implicated in cerebral post-ischemic leukocyte accumulation and activation (R. M. Ransohoff et al., Trends Neurosci., 21, 154, 1998). In fact, systemic increases of CXCL8 have been reported in patients with ischemic stroke and an analogous transient increase in CINC, a CXCL8-like rat neutrophil chemokine related to CXCL8 in humans, was seen in ischemic brain areas (Y. Yamasaki et al., Stroke, 16, 318, 1995). Several neuroprotection studies using the anti-CXCL8 antibody approach, have been successful in rabbit and rat, confirming the potential of therapy targeting CXCL8 in cerebral ischemia (T. Matsumoto et al., Lab. Invest., 77, 119, 1997, Y. Yamasaki et al., Brain Res., 759, 103, 1997, S. Yamagami et al., J. Leukoc. Biol., 65, 744, 1999).

Targeting chemokines and/or their receptors is a promising approach also in the treatment of chronic inflammatory disorders like rheumatoid arthritis (RA), inflammatory bowel disease, multiple sclerosis and transplant rejections. A complex network of adhesion molecules and chemokines coordinate cell migration, by working in concert to induce an inflammatory response and several studies have explored the role of chemokines receptors in the pathogenesis of chronic diseases (J. J. Haringman et al., Ann. Rheum. Dis., 63, 1186, 2004).

The involvement of various chemokines has been also reported in the pathogenesis of several dermatoses like Bullous Pemphigoid (BP), a sub epidermal blistering disease associated with production of autoantibodies to the hemidesmosomal 180 KD BP autoantigen (BP 180). Among them CXCL8 has been implicated in the inflammatory process of both human and experimental murine BP. High levels of CXCL8 were detected in skin lesions or sera of BP patients and, in an experimental mouse model of BP, CXCL8 injections facilitated blister formation in C5- or mast cell-deficient mice otherwise resistant to the induction of blisters (Z. Liu et al., J. Clin. Invest., 95, 1539, 1995). In addition it was demonstrated that antibodies to BP180 mediate a dose- and time-dependent release of CXCL8 from cultured normal epidermal keratinocytes (E. Schmidt et al., J. Invest. Dermatol. 115, 842, 2000).

As reported, the biological activity of CXCL8 is mediated by the interaction of CXCL8 with CXCR1 and CXCR2 membrane receptors belonging to the family of seven transmembrane receptors and expressed on the surface of human neutrophils and of several types of T-cells (L. Xu et al., J. Leukocyte Biol., 57, 335, 1995). Although CXCR1 activation is known to play a crucial role in CXCL8-mediated chemotaxis, it has been recently supposed that also CXCR2 activation could play a pathophysiological role in chronic inflammatory diseases. RA is a chronic systemic inflammatory disorder that attacks principally the joints causing a proliferative synovitis that often progresses to the destruction of the articular cartilage and ankylosis of the joints. Activated T-cells, monocytes/macrophages and neutrophils (PMN) are the predominant cell types involved in synovial inflammation. Leukocyte extravasation through the endothelial barrier into the synovial tissue and synovial fluid is considered a crucial event in the pathogenesis of RA (Z. Szekanecz et al., J. Invest. Med., 44, 124, 1996). Increased cell trafficking is caused by an enhanced expression of pro-inflammatory mediators (cytokines and chemokines) and of adhesion molecules (Z. Szekanecz et al., Sem. Immunol., 15, 15, 2003). In particular, several chemotactic cytokines have been directly implicated in the recruitment and activation of PMNs and mononuclear cells during RA development. The specific pathogenic role of CXCL8, CXCL5, CXCL1 and CXCL6 in RA synovitis has been clearly demonstrated and is clearly associated to the specific role of CXC chemokines in neutrophil recruitment and also in the promotion of angiogenesis. To date, several studies support the concept that CXCL8 and CXCL1 are major mediators of inflammation and joint destruction in RA and elevated levels of these chemokines are detected in the synovial tissues and fluids of RA patients (A. E. Koch et al., J. Immunol., 147, 2187, 1991). Similar evidences have been collected in several animal models and in a model of acute arthritis induced by rabbit knee joint injection of LPS or monosodium urate crystals, the recruitment of PMNs was blocked by treatment with a neutralizing CXCL8-specific antibody with a contemporary protection from joint swelling and tissue damage (P. L. Podolin et al., J. Immunol. 169, 6435, 2002). In contrast to reagents that neutralize the activity of a single chemokine, the antagonist of a multiligand receptor, such as CXCR2, could block the activity of all the mediators acting through the receptor, partially overcoming the redundancy of the system and thus inducing more profound biological effects (K. J. Katschke et al., Arthritis Rheum., 44, 1022, 2001).

Studies on the contribution of single (S) and (R) enantiomers of ketoprofen to the anti-inflammatory activity of the racemate and on their role in the modulation of the chemokine demonstrated (P. Ghezzi et al., J. Exp. Pharm. Ther., 287, 969, 1998) that the two enantiomers and their salts can inhibit in a dose-dependent way the chemotaxis and increase in intracellular concentration of $Ca^{2+}$ ions induced by CXCL8 on human PMN leukocytes (EP0935961). It has been subsequently demonstrated (C. Bizzarri et al., Biochem. Pharmacol. 61, 1429, 2001) that ketoprofen shares the inhibition activity of the biological activity of CXCL8 with other molecules belonging to the class of non-steroidal anti-inflammatory (NSAIDs) such as flurbiprofen and ibuprofen. Racemic mixtures, (R) and (S) enantiomers of 2-arylpropionic acids were demonstrated CXCL8-induced PMN chemotaxis and PMN degranulation inhibitors (WO 03/043625), without any activity on COXs. The compounds of the invention, both as racemic mixtures and (S) enantiomers, are still devoid of any activity on COXs, but, substituted in the 4 position of the phenyl ring with substituted heterocycles, like 2-aminothiazoles or 2-aminooxazoles, are much more potent in the inhibition of CXCL8-induced chemotaxis (active in the low nanomolar range) if compared with the compounds previously described (active in the micromolar range). (R) amides and (R) sulfonamides (WO 01/58852 and WO 00/24710) were described as effective inhibitors of CXCL8-induced chemotaxis in PMNs.

We have now surprisingly found out that also (S) amides and (S) sulfonamides derivatives of 2-arylpropionic acids, opportunely substituted in the 4 position of the phenyl ring with substituted heterocycles, like 2-aminothiazoles or 2-aminooxazoles, share a good biological activity in inhibiting PMN CXCL8-induced chemotaxis.

DETAILED DESCRIPTION OF THE INVENTION

The new molecules belong to a novel class of 2-aryl-propionic acids and derivatives substituted in the 4 position by 2-amino-heterocycles. By the introduction of the substituents below described for compounds of formula (I), also (S) amides and (S) sulfonamides, derived from the parent carboxylic acids, are good CXCL8-induced chemotaxis inhibitors. This aspect is surprising, due to the generally observed lack of CXCL8 inhibition activity of (S)-2-aryl-propanamides belonging to other chemical classes of already claimed compounds (WO 01/58852 and WO 00/24710).

The present invention thus provides (R,S)-2-aryl-propionic acids and derivatives of formula (I):

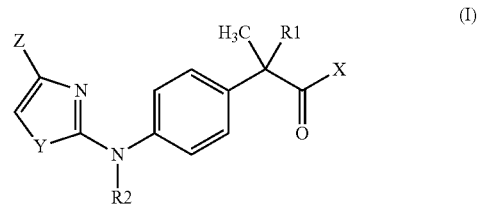

and their single (S) enantiomers,
and pharmaceutically acceptable salts thereof,
wherein
   $R_1$ is selected from
   H and $CH_3$;
   X is OH or a residue of formula $NHR_3$
   wherein
   $R_2$ is selected from
   H and linear C1-C4-alkyl;
   $R_3$ is selected from
   H, OH, $C_1$-$C_5$-alkyl, $C_3$-$C_6$-cycloalkyl, $C_2$-$C_5$-alkenyl, $C_1$-$C_5$-alkoxy;
   straight or branched $C_1$-$C_6$-alkyl, $C_3$-$C_6$-cycloalkyl, $C_2$-$C_6$-alkenyl, $C_1$-$C_6$-phenylalkyl, substituted with a carboxy (COOH) group;
   a residue of formula $SO_2R_4$ wherein $R_4$ is $C_1$-$C_2$-alkyl, $C_3$-$C_6$-cycloalkyl, $C_1$-$C_3$-halo alkyl;
   Y is a heteroatom selected from
   S, O and N
   Z is a residue selected from
   halogen, linear or branched C1-C4-alkyl, C2-C4-alkenyl, C2-C4-alkynyl, C1-C4-alkoxy, hydroxy, carboxyl, C1-C4-acyloxy, phenoxy, cyano, nitro, amino, C1-C4-acylamino, halo-C1-C3-alkyl, halo-C1-C3-alkoxy, benzoyl, linear or branched C1-C8-alkanesulfonate, linear or branched C1-C8-alkanesulfonamides, linear or branched C1-C8 alkyl sulfonylmethyl.

Preferred compounds according to the invention are those wherein:
   $R_1$ is $CH_3$;
   $R_2$ is selected from
   H and $CH_3$;
   X is OH;
   Y is selected from
   S and O
   Z is selected from
   halogen, linear or branched C1-C4-alkyl, C2-C4-alkenyl, C1-C4-acyloxy, phenoxy, cyano, nitro, halo-C1-C3-alkyl, benzoyl, linear or branched C1-C8-alkanesulfonate, linear or branched C1-C8-alkanesulfonamides.

Preferred compounds of the invention are:
1—2-[4-(4-trifluoromethylthiazol-2-yl)aminophenyl]propionic acid;

2—2-methyl-2-(4-{[4-(trifluoromethyl)-1,3-thiazo-2-yl]amino}phenyl)propanoic acid;
3—(2S)-2-(4-{[4-(trifluoromethyl)-1,3-thiazol-2-yl]amino}phenyl)propanoic acid;
3a—(2S)-2-(4-{[4-(trifluoromethyl)-1,3-thiazol-2-yl]amino}phenyl)propanoic acid sodium salt;
4—2-{4-[(4-methyl-1,3-thiazol-2-yl)amino]phenyl}propanoic acid;
5—(2S)-2-{4-[(4-methyl-1,3-thiazol-2-yl)amino]phenyl}propanoic acid;
6—2-{4-[(4-tert-butyl-1,3-thiazol-2-yl)amino]phenyl}propanoic acid;
7—(2S)-2-{4-[(4-tert-butyl-1,3-thiazol-2-yl)amino]phenyl}propanoic acid;
8—2-(4-{methyl[4-(trifluoromethyl)-1,3-thiazo-2-yl]amino}phenyl)propanoic acid;
9—(2S)-2-(4-{methyl[4-(trifluoromethyl)-1,3-thiazol-2-yl]amino}phenyl)propanoic acid;
10—(2S)—N-hydroxy-2-(4-{[4-(trifluoromethyl)-1,3-oxazol-2-yl]amino}phenyl)propanamide;
11—(2S)—N-(methylsulfonyl)-2-(4-{[4-(trifluoromethyl)-1,3-thiazol-2-yl]amino}phenyl)propanamide;
12—(2S)—N-[(trifluoromethyl)sulfonyl]-2-(4-{[4-(trifluoromethyl)-1,3-thiazol-2-yl]amino}phenyl)propanamide;
13—(2S)-2-(4-{[4-(trifluoromethyl)-1,3-thiazol-2-yl]amino}phenyl propanamide;
14—(2S)-2-(4-{methyl[4-(trifluoromethyl)-1,3-thiazol-2-yl]amino}phenyl)propanamide;
15—(2S)-2-{4-[(4-tert.butyl-1,3-thiazol-2-yl)amino]phenyl}propanamide;
16—(2R)-2-{[(2S)-2-(4-{[4-(trifluoromethyl)-1,3-thiazol-2-yl]amino}phenyl)propanoyl]amino}propanoic acid;
17—(2S)-3-methyl-2-{[(2S)-2-(4-{[4-(trifluoromethyl)-1,3-thiazol-2-yl]amino}phenyl)propanoyl]amino}butanoic acid;
18—2-{4-[(4-trifluoromethyl)-oxazol-2-yl]amino}phenyl propionic;
19—(2R)-2-(4-{[4-(trifluoromethyl)-1,3-oxazo-2-yl]amino}phenyl)propanoic acid;
20—(2S)-2-(4-{methyl[4-(trifluoromethyl)-1,3-oxazol-2-yl]amino}phenyl)propanoic acid;
21—(2S)—N-(methylsulfonyl)-2-(4-{[4-(trifluoromethyl)-1,3-oxazol-2-yl]amino}phenyl)propanamide;
22—(2S)-2-(4-{[4-(trifluoromethyl)-1,3-oxazol-2-yl]amino}phenyl)propanamide;
23—(2S)-2-(4-{methyl-[4-(trifluoromethyl)-1,3-oxazol-2-yl]amino}phenyl)propanamide;
24—(2S)-2-{[(2S)-2-(4-{[4-(trifluoromethyl)-1,3-oxazol-2-yl]amino}phenyl)propanoyl]amino}propanoic acid;
25—(2S)—N-[(1S)-2- amino-1-methyl-2-oxoethyl]-2-(4-{[4-(trifluoromethyl)-1,3-oxazol-2-yl]amino}phenyl)propanamide.

Most preferred compounds in the list are compound 3 [(2S)-2-(4-{[4-(trifluoromethyl)-1,3-thiazol-2-yl]amino}phenyl)propanoic acid] and the related sodium salt 3a.

The compounds of the invention of formula (I) are generally isolated in the form of their addition salts with both organic and inorganic pharmaceutically acceptable bases. Examples of such bases are: sodium hydroxide, potassium hydroxide, calcium hydroxide, (D,L)-Lysine, L-Lysine, tromethamine.

The compounds of the invention of formula (I) were evaluated in vitro for their ability to inhibit chemotaxis of polymorphonucleate leukocytes (hereinafter referred to as PMNs) and monocytes induced by the fractions of CXCL8 and GRO-α. For this purpose, in order to isolate the PMNs from heparinized human blood, taken from healthy adult volunteers, mononucleates were removed by means of sedimentation on dextran (W. J. Ming et al., J. Immunol., 138, 1469, 1987). The cell vitality was calculated by exclusion with Trypan blue, whilst the ratio of the circulating polymorphonucleates was estimated on the cytocentrifugate after staining with Diff Quick.

In the CXCL8 induced chemotaxis assay human recombinant CXCL8 (Pepro Tech) was used as stimulating agent in the chemotaxis experiments: the lyophilized protein was dissolved in a volume of HBSS containing 0.2% bovin serum albumin (BSA) in order to obtain a stock solution having a concentration of $10^{-5}$ M to be diluted in HBSS to a concentration of $10^{-9}$ M, for the chemotaxis assays.

GRO-α induced chemotaxis inhibition was evaluated in an analogous assay.

In the chemotaxis experiments, the PMNs were incubated with the compounds of the invention of formula (I) for 15' at 37° C. in an atmosphere containing 5% $CO_2$. During the chemotaxis assay (W. Falket et al., J. Immunol. Methods, 33, 239, 1980) PVP-free filters with a porosity of 5 µm and microchambers suitable for replication were used.

The compounds of the invention in formula (I) were evaluated at a concentration ranging between $10^{-6}$ and $10^{-10}$ M; for this purpose they were added, at the same concentration, both to the lower pores and the upper pores of the microchamber. Evaluation of the ability of the compounds of the invention of formula (I) to inhibit the chemotaxis of human monocytes was carried out according to a disclosed method (J. Van Damme et al., Eur. J. Immunol., 19, 2367, 1989).

All the compounds of the invention demonstrated a high degree of selectivity towards the inhibition of the CXCL8 induced chemotaxis compared to the chemotaxis induced by C5a ($10^{-6}$ M) or f-MLP ($10^{-6}$ M).

The compounds of formula (I), evaluated ex vivo in the blood in toto according to a disclosed procedure (Patrignani et al., J. Pharmacol. Exper. Ther., 271, 1705, 1994) were found to be totally ineffective as inhibitors of cyclooxygenase enzymes. In fact, the compounds of the invention do not interfere with the production of $PGE_2$ in murine macrophages stimulated with lipopolysaccharides (LPS, 1 µg/ml) over the concentration range of $10^{-5}$ to $10^{-6}$ M.

Due to the absence of COX inhibitory activity in racemates and (S) enantiomers of the described 2-aryl-propionic acids and derivatives, the compounds of the invention represent novel examples of 2-aryl-propionic acids and derivatives with the necessary features for a therapeutical use in pathologies related to exacerbated neutrophil chemotaxis and activation induced by CXCL8.

It's therefore a further object of the invention the use of compounds of formula (I) in the treatment of diseases the involve CXCL8 induced human PMNs chemotaxis.

The compounds of the present invention are particularly useful in the prevention and treatment of damages caused by ischemia/reperfusion, specifically in the protection from the functional injury induced by temporary cerebral middle cerebral artery (MCA) occlusion. Specifically, compound 3a was evaluated in terms of efficacy in a model of transient cerebral ischemia induced in rats by occlusion of the middle cerebral artery (MCA). The short-term effect (24 hours) of 3a on cerebral myeloperoxidase (MPO) activity, a marker of PMN infiltration, brain damage and neurological deficits, was investigated. The compound was efficacious in reducing PMN infiltrate, infarct size and in improving significantly neurological functions.

More, in view of the experimental evidence discussed above and of the role performed by CXCL8 and congenetics thereof in the processes involving the activation and the infiltration of neutrophils, the compounds of the invention are effective in the treatment of chronic diseases such as Bullous Pemphigoid, Rheumatoid Arthritis (M. Selz et al., J. Clin. Invest., 87, 463, 1981), idiopathic fibrosis (E. J. Miller, previously cited, and P. C. Carré et al., J. Clin. Invest., 88, 1882, 1991) and glomerulonephritis (T. Wada et al., J. Exp. Med., 180, 1135, 1994).

It is therefore a further object of the present invention to provide the use of compounds of formula (I) in the treatment of damages caused by ischemia and reperfusion, bullous pemphigo, rheumatoid arthritis, idiopathic fibrosis, glomerulonephritis and, particularly, the use in the treatment of transient cerebral ischemia.

Pharmaceutical compositions comprising a compound of the invention and a suitable carrier thereof, are also within the scope of the present invention.

The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the acids of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like.

Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the acid derivative of formula I in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18$^{th}$ Edition, 1990, Mack Publishing Company, Easton, Pa., which is incorporated herein by reference.

The compounds of the invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

The preparation of the compounds of formula (I) was carried out using known synthetic methods both for the acids and for the related amides and acylsulfonamides. The key intermediates for racemic and (S) enantiomer compounds are racemic and (S) enantiomer methyl 2-[4-(carbamothioylamino)phenyl]propanoate and methyl 2-[4-(carbamoylamino)phenyl]propanoate that were transformed into the related 4-heterocycle derivatives, hydrolysed to carboxylic acids and, subsequently, coupled with sulfonamides and amines to afford compounds of formula (I).

EXPERIMENTAL SECTION

List of Abbreviations $CH_2Cl_2$: dichloromethane; $CHCl_3$: chloroform; $Et_2O$: diethyl ether; AcOH: acetic acid; THF: tetrahydrofuran; LiHMDS: lithium hexamethyldisilazide; CDI: 1,1'-carbonyldiimidazole; $SOCl_2$: thionyl chloride; TEA: triethylamine.

Preparation of Intermediates

Methyl (2S)-2-(4-aminophenyl)propanoate is obtained by optical resolution of commercial racemic 2-(4-nitrophenyl) propanoic acid according a known procedure (Akgun H. et al., Arzneim.-Forsch./Drug Res., 46(II), 891, 1996) and subsequent reduction of the nitro group to amine with Fe/HCl in methanol.

Methyl 2-(4-aminophenyl)propanoate is obtained directly by reduction of 2-(4-nitrophenyl)propanoic acid with Fe/HCl in methanol.

(S)-Methyl 2-[4-(carbamothioylamino)phenyl]propanoate

In a 500 ml round-bottomed flask equipped with condenser and magnetic stirrer, at room temperature methyl (2S)-2-(4-aminophenyl)propanoate (17.5 g, 98 mmol) was dissolved in toluene (300 ml) and conc. $H_2SO_4$ (2.6 mmol, 50 mmol) was slowly added to the solution Sodium thiocyanate (10.29 g, 128 mmol) was added and the reaction mixture refluxed 24 h. After cooling at room temperature, the solution was washed with a saturated solution of $NH_4Cl$ (2×100 ml), dried over anhydrous $Na_2SO_4$ and evaporated under vacuum to give a crude which, after purification by flash chromatography (n-hexane/EtOAc 1/1), afforded pure (S)-methyl 2-[4-(carbamothioylamino)phenyl]propanoate (10.7 g, 48.4 mmol) as white solid (49%). $^1$H-NMR (CDCl$_3$): δ 8.25 (bs, 1H, CSNH), 7.40 (d, 2H, J=7 Hz), 7.20 (d, 2H, J=7 Hz), 6.20 (bs, 2H, CSNH$_2$), 3.75 (m, 1H), 3.65 (s, 3H), 1.50 (d, 3H, J=7 Hz).

(S)-Methyl 2-[4-(carbamoylamino)phenyl]propanoate

Following the same procedure described for (S)-methyl 2-[4-(carbamothioylamino)phenyl]propanoate and starting from methyl (2S)-2-(4-aminophenyl)propanoate (98 mmol) and sodium cyanate (128 mmol), after workup (S)-methyl 2-[4-(carbamoylamino)phenyl]propanoate was isolated as white solid (59%). $^1$H-NMR (CDCl$_3$): δ 8.90 (bs, 1H, CONH), 7.55 (d, 2H, J=7 Hz), 7.20 (d, 2H, J=7 Hz), 6.50 (bs, 2H, CONH$_2$), 3.75 (m, 1H), 3.60 (s, 3H), 1.50 (d, 3H, J=7 Hz).

Methyl 2-[4-(carbamothioylamino)phenyl]propanoate

Following the same procedure described for (S)-methyl 2-[4-(carbamothioylamino)phenyl]propanoate and starting from methyl 2-(4-aminophenyl)propanoate (98 mmol), after workup methyl 2-[4-(carbamoylamino)phenyl]propanoate was isolated as white solid (74%). $^1$H-NMR (CDCl$_3$): δ 8.25 (bs, 1H, CSNH), 7.40 (d, 2H, J=7 Hz), 7.20 (d, 2H, J=7 Hz), 6.20 (bs, 2H, CSNH$_2$), 3.75 (m, 1H), 3.65 (s, 3H), 1.50 (d, 3H, J=7 Hz).

Methyl 2-[4-(carbamoylamino)phenyl]propanoate

Following the same procedure described for (S)-methyl 2-[4-(carbamothioylamino)phenyl]propanoate and starting from methyl 2-(4-aminophenyl)propanoate (98 mmol) and sodium cyanate (128 mmol), after workup methyl 2-[4-(carbamoylamino)phenyl]propanoate was isolated as white solid (65%). $^1$H-NMR (CDCl$_3$): δ 8.90 (bs, 1H, CONH), 7.55 (d, 2H, J=7 Hz), 7.20 (d, 2H, J=7 Hz), 6.50 (bs, 2H, CONH$_2$), 3.75 (m, 1H), 3.60 (s, 3H), 1.50 (d, 3H, J=7 Hz).

EXAMPLES

2-(4-{[4-(Trifluoromethyl)-1,3-thiazol-2-yl]amino}phenyl)propanoic acid (1)

In a 250 ml round-bottomed flask equipped with condenser and magnetic stirrer, a solution of methyl 2-[4-(carbamothioylamino)phenyl]propanoate (10.7 g, 48.4 mmol) in 1,4-dioxane (200 ml) was treated at room temperature with 3-bromo-1,1,1-trifluoro-propan-2-one (5 ml, 48.4 mmol) and the reaction mixture was refluxed for 2 h. After cooling at room temperature, the solvent was distilled under vacuum, the residue dissolved in $CH_2Cl_2$ (200 ml), washed with a saturated solution of $NaHCO_3$ (3×100 ml), dried over anhydrous $Na_2SO_4$ and evaporated under vacuum to give pure methyl 2-(4-{[4-(trifluoromethyl)-1,3-thiazol-2-yl]amino}phenyl)propanoate (12.8 g, 38.7 mmol) as yellow oil (80%).

$^1$H-NMR (CDCl$_3$): δ 8.65 (s, 1H, NH), 7.30 (m, 4H), 7.05 (s, 1H), 3.75 (q, 1H, J=7 Hz), 3.65 (s, 3H), 1.50 (d, 3H, J=7 Hz).

A solution of methyl 2-(4-{[4-(trifluoromethyl)-1,3-thiazo-2-yl]amino}phenyl)propanoate (12 g, 36.28 mmol) in AcOH (50 ml) and 37% HCl (17.5 ml) was refluxed for 12 h. After cooling at room temperature, solvents were evaporated and the crude dissolved in $CH_2Cl_2$ (200 ml) and washed with water (3×100 ml) and brine (3×100 ml). The organic layer was dried over anhydrous $Na_2SO_4$ and the solvent evaporated under vacuum. The resulting pale yellow oil was pulped in n-hexane (150 ml) overnight. Pure compound 1 (7.8 g, 24.67 mmol) was obtained as a white solid by filtration (68% from the methyl ester intermediate).

$^1$H-NMR (CDCl$_3$): δ 9.25 (bs, 1H, NH), 7.40 (d, 2H, J=7 Hz), 7.25 (d, 2H, J=7 Hz), 7.00 (s, 1H), 3.80 (q, 1H, J=7 Hz), 1.55 (d, 3H, J=7 Hz).

2-Methyl-2-(4-{[4-(trifluoromethyl)-1,3-thiazol-2-yl]amino}phenyl)propanoic acid (2)

Trifluoroacetylchloride (3 mmol) was bubbled into a mixture of 2-(4-{[4-(trifluoromethyl)-1,3-thiazol-2-yl]amino}phenyl) propanoate (0.5 g, 1.5 mmol) and $K_2CO_3$ (0.41 g, 3.0 mmol) in dry THF (5 ml). The reaction mixture was refluxed for 4 h. After disappearance of the starting material and cooling at room temperature, THF was evaporated under vacuum and the residue dissolved in $CH_2Cl_2$ (10 ml) and in buffer $H_3PO_4/H_2PO_4^-$ solution (pH=2.0, 10 ml). The mixture was transferred into a reparatory funnel, the two phases separated and the organic one washed again with the same buffer (3×5 mL), dried over $Na_2SO_4$ and evaporated under vacuum to give pure methyl 2-(4-{(trifluoroacetyl)[4-(trifluoromethyl)-1,3-thiazol-2-yl]amino}phenyl)propanoate (0.60 gr, 1.4 mmol) as a transparent oil (94%).

LiHMDS was prepared by treatment of 1,1,1,3,3,3-hexamethyldisilazane (64 mmol) with n-BuLi (1.6 M in n-hexane, 63 mmol) according known procedures. To a solution of LiHMDS (1.4 mmol) in dry THF (5 ml) at T=−78° C., a solution of 2-(4-{(trifluoroacetyl)[4-(trifluoromethyl)-1,3-thiazol-2-yl]amino}phenyl)propanoate (0.60 gr, 1.4 mmol) in dry THF (2 ml) was added dropwise; the resulting mixture was left stirring for 1 h, iodomethane (62 µl, 1.5 mmol) was added and the solution left stirring at room temperature overnight. Et$_2$O (10 ml) and a buffer $H_3PO_4/H_2PO_4^-$ solution (pH=2.0, 10 ml) were added. The phases were separated and the aqueous one extracted back with Et$_2$O (3×5 mL); the collected organic extracts were dried over anhydrous $Na_2SO_4$ and evaporated under vacuum to give a crude that, after purification by flash chromatography, afforded pure methyl 2-methyl-2-(4-{(trifluoroacetyl)[4-(trifluoromethyl)-1,3-thiazol-2-yl]amino}phenyl)propanoate (0.40 gr, 0.91 mmol) as yellow oil (65%).

To a solution of the methyl ester in THF (5 ml), 1M NaOH (2.0 ml) was added and the reaction mixture was refluxed overnight. After cooling at room temperature, the mixture was quenched with a buffer $H_3PO_4/H_2PO_4^-$ solution (pH=2.0, 5 ml) and trasferred into a reparatory funnel. The phases were separated, the aqueous one extracted with $CH_2Cl_2$ (3×5 mL), the collected organic extracts dried over $Na_2SO_4$ and evaporated under vacuum to give pure compound 2 (0.29 g, 0.88 mol) as waxy yellow solid (97%).

$^1$H-NMR (CDCl$_3$): δ 12.20 (bs, s, COOH), 9.25 (bs, 1H, NH), 7.40 (d, 2H, J=7 Hz), 7.25 (d, 2H, J=7 Hz), 7.00 (s, 1H), 1.55 (s, 6H).

(2S)-2-(4-{[4-(Trifluoromethyl)-1,3-thiazol-2-yl]amino}phenyl)propanoic acid (3)

Following the same procedure described for 1 and starting from (S)-methyl 2-[4-(carbamothioylamino)phenyl]propanoate (10.7 g, 48.4 mmol), after workup and methyl ester hdrolysis, compound 3 (12.24 g, 38.72 mmol) was isolated as a white solid (80%).

$[α]_D$=+37 (c=1.2; CH$_3$OH); $^1$H-NMR (CDCl$_3$): δ 9.25 (bs, 1H, NH), 7.40 (d, 2H, J=7 Hz), 7.25 (d, 2H, J=7 Hz), 7.00 (s, 1H), 3.80 (q, 1H, J=7 Hz), 1.55 (d, 3H, J=7 Hz).

Sodium (2S)-2-(4-{[4-(trifluoromethyl)-1,3-thiazol-2-yl]amino}phenyl)propanoate (3a)

In a 100 ml round-bottomed flask equipped with a magnetic stirrer, compound 3 (7.26 gr, 22.9 mmol) was suspended in water (30 ml) and 2N NaOH (11.45 ml, 22.9 mol) was slowly added. The resulting dark red solution was stirred for 1 h at room temperature, filtered on a 0.45μ filter and freeze dried. Pure sodium (2S)-2-(4-{[4-(trifluoromethyl)-1,3-thiazol-2-yl]amino}phenyl)propanoate 3a (7.51 g, 22.2 mmol) was obtained as white solid (97%). m.p. 142°-145° C. $[α]_D$=−8.7 (c=0.62; CH$_3$OH); $^1$H-NMR (D$_2$O): δ 9.00 (bs, 1H, NH), 7.30 (m, 4H), 7.28 (s, 1H), 3.55 (q, 1H, J=7 Hz), 1.35 (d, 3H, J=7 Hz).

2-{4-[(4-Methyl-1,3-thiazol-2-yl)amino]phenyl}propanoic acid (4)

Following the same procedure described for 1 and starting from methyl 2-[4-(carbamothioylamino)phenyl]propanoate (4.98 g, 20 mmol) and 1-chloro-propan-2-one (2.13 ml, 26 mmol), after workup and methyl ester hydrolysis pure compound 4 (2.5 g, 9.5 mmol) was isolated by filtration (49% overall yield from methyl 2-[4-(carbamothioylamino)phenyl]propanoate).

$^1$H-NMR (DMSO-d$_6$): δ 9.25 (bs, 1H, NH), 7.45 (d, 2H, J=7 Hz), 7.30 (d, 2H, J=7 Hz), 6.60 (s, 1H), 3.65 (q, 1H, J=7 Hz), 2.25 (s, 3H), 1.35 (d, 3H, J=7 Hz).

(2S)-2-{4-[(4-Methyl-1,3-thiazol-2-yl)amino]phenyl}propanoic acid (5)

Following the same procedure described for 4 and starting from (5)-methyl 2-[4-(carbamothioylamino)phenyl]propanoate (10 g, 45.23 mmol), after workup and methyl ester hydrolysis compound 5 (10.72 g, 33.9 mmol) was isolated as a white solid (75%).

$[α]_D$=+20 (c=0.2; CH$_3$OH); $^1$H-NMR (DMSO-d$_6$): δ 9.25 (bs, 1H, NH), 7.45 (d, 2H, J=7 Hz), 7.30 (d, 2H, J=7 Hz), 6.60 (s, 1H), 3.65 (q, 1H, J=7 Hz), 2.25 (s, 3H), 1.35 (d, 3H, J=7 Hz).

2-{4-[(4-tert-Butyl-1,3-thiazol-2-yl)amino]phenyl}propanoic acid (6)

Following the same procedure described for 1 and starting from methyl 2-[4-(carbamothioylamino)phenyl]propanoate (2.49 g, 10 mmol) and 1-bromopinacolone (1.75 ml, 13 mmol), after workup and methyl ester hydrolysis, pure compound 6 (1.75 g, 5.7 mmol) was isolated by filtration (38% overall yield from methyl 2-[4-(carbamothioylamino)phenyl]propanoate).

$^1$H-NMR (DMSO-d$_6$): δ 9.20 (bs, 1H, NH) 7.55 (d, 2H, J=7 Hz), 7.20 (d, 2H, J=7 Hz), 6.45 (s, 1H), 3.60 (q, 1H, J=7 Hz), 1.35 (d, 3H, J=7 Hz), 1.25 (s, 9H).

(2S)-2-{4-[(4-tert-Butyl-1,3-thiazol-2-yl)amino]phenyl}propanoic acid (7)

Following the same procedure described for 6 and starting from (S)-methyl 2-[4-(carbamothioylamino)phenyl]propanoate (10 g, 45.23 mmol), after workup and methyl ester hydrolysis, compound 7 (11.14 g, 36.6 mmol) was isolated as a white solid (81%).

$[α]_D$=+25.8 (c=1; CH$_3$OH); $^1$H-NMR (DMSO-d$_6$): δ 9.20 (bs, 1H, NH) 7.55 (d, 2H, J=7 Hz), 7.20 (d, 2H, J=7 Hz), 6.45 (s, 1H), 3.60 (q, 1H, J=7 Hz), 1.35 (d, 3H, J=7 Hz), 1.25 (s, 9H).

2-(4-{Methyl[4-(trifluoromethyl)-1,3-thiazol-2-yl]amino}phenyl)propanoic acid (8)

To a solution of intermediate methyl 2-(4-{[4-(trifluoromethyl)-1,3-thiazol-2-yl]amino}phenyl)propanoate (0.1 g, 0.303 mmol) and CsOH*H$_2$O (0.046 g, 2.75 mmol) in dry CH$_2$Cl$_2$ (5 ml), iodomethane was added (17.5 μl, 0.275 mmol) and the reaction mixture was left stirring overnight at room temperature. After quenching by buffer $H_3PO_4/H_2PO_4^-$ solution (pH=2.0, 10 ml), the reaction mixture was trasferred into a separatory funnel, the two phases separated and the aqueous one extracted with CH$_2$Cl$_2$ (3×10 mL); the collected organic extracts were dried over Na$_2$SO$_4$ and evaporated under vacuum to give a crude which, after purification by flash chromatography, afforded pure methyl 2-(4-{methyl[4-(trifluoromethyl)-1,3-thiazol-2-yl]amino}phenyl) propanoate (0.074 g, 0.215 mol) as a yellow oil (71%).

To a solution of the methyl ester in THF (5 ml), 1M NaOH (1.4 ml) was added and the reaction mixture was stirred overnight at room temperature. After quenching with a buffer $H_3PO_4/H_2PO_4^-$ solution (pH=2.0, 5 ml), the reaction mixture was transferred into a separatory funnel, the two phases were separated and the aqueous layer was extracted with CH$_2$Cl$_2$ (3×5 mL); the collected organic extracts were dried over Na$_2$SO$_4$ and evaporated under vacuum to give pure compopund 8 (0.070 g, 0.214 mol) as pale yellow solid (97%).

$^1$H-NMR (DMSO-d$_6$): δ 7.50-7.30 (m, 5H); 3.70 (q, 1H, J=7 Hz); 3.45 (s, 3H); 1.35 (d, 3H, J=7 Hz).

(2S)-2-(4-{methyl[4-(trifluoromethyl)-1,3-thiazol-2-yl]amino}phenyl)propanoic acid (9)

Following the same procedure described for 8 and starting from methyl (2S)-2-(4-{[4-(trifluoromethyl)-1,3-thiazol-2-yl]amino}phenyl)propanoate (0.1 g, 0.303 mmol), after workup compound 9 (0.055 g, 0.168 mmol) was isolated as yellow glassy solid (55%).

$[α]_D$=+21 (c=0.5; CH$_3$OH); $^1$H-NMR (DMSO-d$_6$): δ 7.50-7.30 (m, 5H); 3.70 (q, 1H, J=7 Hz); 3.45 (s, 3H); 1.35 (d, 3H, J=7 Hz).

(2S)—N-Hydroxy-2-(4-{[4-(trifluoromethyl)-1,3-thiazol-2-yl]amino}phenyl) propanamide (10)

In a 25 ml round-bottomed flask equipped with a magnetic stirrer a solution of hydroxylamine hydrochloride (0.046 g, 0.66 mmol) and TEA (121 μl, 0.88 mmol) in CHCl₃ (2 ml) was stirred at room temperature for 15 min.

Separately, a solution of compound 3 (0.070 g, 0.22 mmol) in SOCl₂ (3 ml) was refluxed for 3 h. After cooling at room temperature, excess SOCl₂ was distilled off under vacuum and the crude acyl chloride diluted with CHCl₃ (5 ml) and slowly added by dripping to the hydroxylamine solution at T=0° C. After ice bath removal, the reaction mixture was stirred for additional 2.5 h, then was diluted in CHCl₃ (30 ml), washed with 10% KHSO₄ (3×10 ml), brine (3×10 ml) and dried over anhydrous Na₂SO₄ to give a crude which, after purification by flash chromatography, afforded pure compound 10 (0.050 g, 0.15 mmol) as a white waxy solid (68%).

$[\alpha]_D$=+23.5 (c=0.5; CH₃OH); ¹H-NMR (DMSO-d₆): δ 10.5 (bs, 1H, NH), 7.60 (s, 1H), 7.45 (d, 2H, J=7 Hz), 7.30 (bs, 1H, OH), 7.25 (d, 2H, J=7 Hz), 6.75 (bs, 1H, CONH), 3.50 (q, 1H, J=7 Hz), 1.40 (d, 3H, J=7 Hz).

(2S)—N-(Methylsulfonyl)-2-(4-{[4-(trifluoromethyl)-1,3-thiazol-2yl]amino}phenyl) propanamide (11)

To a solution of (2S)-2-4-{[4-trifluoromethyl)-1,3-thiazol-2yl]amino}phenyl)propanoic acid (3) (0.1 g, 0.32 mmol) in dry CH₂Cl₂ (2 mL) CDI (0.055 g, 0.34 mmol) was added and the resulting solution was stirred for 1 h at T=0° C. After ice-water bath removal methanesulfonamide (0.032 g, 0.34 mmol) and TEA (40 μl, 0.29 mmol) were added and the resulting mixture was stirred at room temperature for 12 h. At the complete disappearance of the starting material, a buffer $H_3PO_4/H_2PO_4^-$ solution (pH=2.0, 5 ml) was added and the reaction mixture was trasferred into a reparatory funnel. The two phases were separated and the organic one washed with the same buffer (3×5 mL), dried over Na₂SO₄ and evaporated under vacuum to give a crude which was purified by flash chromatography. Pure compound 11 (0.089 g, 0.23 mol) was isolated as a yellow oil (71%).

$[\alpha]_D$=+46.7 (c=0.5; CH₃OH); ¹H-NMR (CDCl₃): δ 8.05 (bs, 1H, NH), 7.55 (bs, 1H, CONH), 7.40 (d, 2H, J=7 Hz), 7.25 (d, 2H, J=7 Hz), 7.10 (s, 1H), 3.65 (q, 1H, J=7 Hz), 3.25 (s, 3H), 1.55 (d, 3H, J=7 Hz).

(2S)—N-[(Trifluoromethyl)sulfonyl]-2-(4-{[4-(trifluoromethyl)-1,3-thiazol-2-yl]amino}phenyl propanamide (12)

Following the same procedure described for 11 and starting from (2S)-2-(4-{[4-(trifluoromethyl)-1,3-thiazol-2-yl]amino}phenyl)propanoic acid (3) (0.1 g, 0.32 mmol) and trifluoromethanesulfonamide (0.051 g, 0.34 mmol), after workup compound 12 (0.078 g, 0.24 mmol) was isolated as white solid (75%).

m.p. 90°-95° C.; $[\alpha]_D$=+32.2 (c=0.5; CH₃OH); ¹H-NMR (DMSO-d₆): δ 10.45 (bs, 1H, NH), 7.60 (s, 1H), 7.45 (d, 2H, J=7 Hz), 7.25 (d, 2H, J=7 Hz), 3.45 (q, 1H, J=7 Hz), 1.25 (d, 3H, J=7 Hz).

(2S)-2-(4-{[4-(Trifluoromethyl)-1,3-thiazol-2-yl]amino}phenyl propanamide (13)

Following the same procedure described for 11 and starting from (2S)-2-(4-{[4-(trifluoromethyl)-1,3-thiazol-2-yl]amino}phenyl)propanoic acid (3) (0.2 g, 0.63 mmol) and anhydrous NH₃, after workup compound 13 (0.19 g, 0.61 mmol) was isolated as pale yellow solid (97%).

m.p. 204°-205° C.; $[\alpha]_D$=+11.25 (c=1; CH₃OH); ¹H-NMR (DMSO-d₆): δ 10.45 (bs, 1H, NH), 7.60 (s, 1H), 7.45 (d, 2H, J=7 Hz), 7.30 (bs, 1H, CONH), 7.25 (d, 2H, J=7 Hz), 6.75 (bs, 1H, CONH), 3.50 (q, 1H, J=7 Hz), 1.30 (d, 3H, J=7 Hz).

(2S)-2-(4-{Methyl[4-(trifluoromethyl)-1,3-thiazol-2-yl]amino}phenyl)propanamide (14)

Following the same procedure described for 13 and starting from (2S)-2-(4-{methyl[4-(trifluoromethyl)-1,3-thiazol-2-yl]amino}phenyl)propanoic acid (9) (0.1 g, 0.30 mmol), after workup compound 14 (0.096 g, 0.29 mmol) was isolated as pale yellow solid (97%).

$[\alpha]_D$=+7.8 (c=0.5; CH₃OH); ¹H-NMR (CDCl₃): δ 7.45-7.30 (m, 4H), 6.85 (s, 1H), 5.35 (bs, 2H, CONH₂), 3.65 (q, 1H, J=7 Hz), 3.55 (s, 3H), 1.55 (d, 3H, J=7 Hz).

(2S)-2-{4-[(4-tert-Butyl-1,3-thiazol-2-yl)amino]phenyl}propanamide (15)

Following the same procedure described for 13 and starting from (2S)-2-{4-[(4-tert-butyl-1,3-thiazol-2-yl)amino]phenyl}propanoic acid (7) (0.1 g, 0.33 mmol), after workup compound 15 (0.097 g, 0.32 mmol) was isolated as white solid like a wax (98%).

$[\alpha]_D$=+10 (c=0.5; CH₃OH); ¹H-NMR (CDCl₃): δ 10.45 (bs, 1H, NH), 7.35 (d, 2H, J=7 Hz), 7.30 (d, 2H, J=7 Hz), 6.20 (s, 1H), 5.30 (bs, 2H, CONH₂), 3.55 (q, 1H, J=7 Hz), 1.55 (d, 3H, J=7 Hz), 1.30 (s, 9H).

(2R)-2-{[(2S)-2-(4-{[4-(Trifluoromethyl)-1,3-thiazol-2-yl]amino}phenyl)propanoyl]amino}propanoic acid (16)

A cooled solution of (2S)-2-(4-{[4-(trifluoromethyl)-1,3-thiazol-2-yl]amino}phenyl)propanoic acid (3) (0.1 g, 0.32 mmol) and CDI (0.054 g, 0.33 mmol) in dry CH₂Cl₂ (5 mL) was stirred for 1 h at T=0-5° C. After ice-water bath removal, a mixture of D-alanine methyl ester hydrochloride (0.045 g, 0.32 mmol) and TEA (90 μl, 0.65 mmol) was added with vigorous stirring and the resulting mixture was stirred overnight at room temperature. At the complete disappearance of the starting material, a buffer $H_3PO_4/H_2PO_4^-$ solution (pH=2.0, 5 ml) was added and the reaction mixture was transferred into a separatory funnel. The two phases were separated and the organic one washed with the same buffer (3×5 mL), dried over Na₂SO₄ and evaporated under vacuum to give a crude which was purified by flash chromatography. Pure methyl (2R)-2-{[(2S)-2-(4-{[4-(trifluoromethyl)-1,3-thiazol-2-yl]amino}phenyl)propanoyl]amino}propanoate (0.1 g, 0.25 mmol) was isolated as a yellow oil (78%).

To a solution of the methyl ester (0.1 gr, 0.25 mol) in 1,4-dioxane (5 ml), 1M NaOH (0.25 ml) was added and the reaction mixture was stirred overnight at room temperature. After quenching with a buffer $H_3PO_4/H_2PO_4^-$ solution (pH=2.0, 5 ml), the reaction mixture was transferred into a separatory funnel, the two phases were separated and the aqueous layer was extracted with CH₂Cl₂ (3×5 mL); the collected organic extracts were dried over Na₂SO₄ and evaporated under vacuum to give pure compound 16 (0.093 g, 0.29 mmol) as white waxy solid (97%).

$[\alpha]_D$=+28.7 (c=0.5; CH₃OH); ¹H-NMR (CDCl₃): δ 9.45 (bs, 1H, NH), 7.30-7.15 (m, 4H), 7.00 (s, 1H), 6.35 (bs, 1H, CONH), 4.45 (m, 1H) 3.50 (q, 1H, J=7 Hz), 1.45 (d, 3H, J=7 Hz), 1.35 (d, 3H, J=7 Hz).

(2S)-3-Methyl-2-{[(2S)-2-(4-{[4-(trifluoromethyl)-1,3-thiazol-2-yl]amino}phenyl) propanoyl]amino}butanoic acid (17)

Following the same procedure described for 16 and starting from (2S)-2-(4-{[4-(trifluoromethyl)-1,3-thiazol-2-yl]

amino}phenyl)propanoic acid (3) (0.18 g, 0.57 mmol) and L-valine methyl ester hydrochloride (0.095 g, 0.57 mmol), after workup compound 17 (0.093 g, 0.23 mmol) was isolated as a white solid (69%).

m.p. 99-101° C.; $^1$H-NMR (CDCl$_3$): δ 10.40 (bs, 1H, NH), 7.45 (d, 2H, J=7 Hz), 7.25 (d, 2H, J=7 Hz), 7.00 (s, 1H), 5.85 (bs, 1H, CONH), 4.70 (m, 1H) 3.75 (q, 1H, J=7 Hz), 2.30 (m, 1H), 1.65 (d, 3H, J=7 Hz), 0.90 (d, 3H, J=7 Hz), 0.75 (d, 3H, J=7 Hz).

2-{4-[(4-Trifluoromethyl)-oxazol-2-yl]amino}phenyl propionic (18)

Following the same procedure described for 1 and starting from the intermediate methyl 2-[4-(carbamoylamino)phenyl]propanoate (10 g, 45 mmol), after workup and methyl ester hydrolysis, compound 18 (9.32 g, 31.05 mmol) was isolated as pale brown oil (69%).

$^1$H-NMR (DMSO-d$_6$): δ 12.45 (bs, 1H, COOH), 10.45 (s, 1H, NH), 8.35 (s, 1H), 7.45 (d, 2H, J=7 Hz); 7.25 (d, 2H, J=7 Hz); 3.70 (m, 1H); 1.25 (d, 3H, J=7 Hz).

(2S)-2-(4-{[4-(Trifluoromethyl)-1,3-oxazol-2-yl]amino}phenyl)propanoic acid (19)

Following the same procedure described for 3 and starting from the intermediate (2S)-methyl 2-[4-(carbamoylamino)phenyl]propanoate (5 g, 22.5 mmol), after workup and methyl ester hydrolysis, compound 19 (3.38 g, 11.25 mmol) was isolated as pale brown oil (50%).

[α]$_D$=+54 (c=0.5; EtOAc); $^1$H-NMR (DMSO-d$_6$): δ 12.45 (bs, 1H, COOH), 10.45 (bs, 1H, NH), 8.35 (s, 1H), 7.45 (d, 2H, J=7 Hz); 7.25 (d, 2H, J=7 Hz); 3.70 (m, 1H); 1.25 (d, 3H, J=7 Hz).

(2S)-2-(4-{Methyl[4-(trifluoromethyl)-1,3-oxazol-2-yl]amino}phenyl)propanoic acid (20)

Following the same procedure described for 9 and starting from methyl (2S)-2-(4-{[4-(trifluoromethyl)-1,3-oxazol-2-yl]amino}phenyl)propanoate (0.1 g, 0.32 mmol), after workup and methyl ester hydrolysis, compound 20 (0.053 g, 0.17 mmol) was isolated as pale brown oil (53%).

[α]$_D$=+38 (c=1; EtOAc); $^1$H-NMR (DMSO-d$_6$): δ 12.45 (bs, 1H, COOH), 8.35 (s, 1H), 7.45-7.25 (m, 4H); 3.80 (m, 1H); 3.40 (s, 3H); 1.40 (d, 3H, J=7 Hz).

(2S)—N-(Methylsulfonyl)-2-(4-{[4-(trifluoromethyl)-1,3-oxazol-2-yl]amino}phenyl) propanamide (21)

Following the same procedure described for 11 and starting from (2S)-2-(4-{[4-(trifluoromethyl)-1,3-oxazol-2-yl]amino}phenyl)propanoic acid (19) (0.1 g, 0.33 mmol), after workup, compound 21 (0.084 g, 0.23 mmol) was isolated as yellow oil (70%).

[α]$_D$=+39 (c=0.5; acetone); $^1$H-NMR (CDCl$_3$): δ 11.25 (bs, 1H, NHSO$_2$CH$_3$); 9.45 (bs, 1H, NH), 7.50 (m, 3H), 7.15 (d, 2H, J=7 Hz); 3.65 (m, 1H); 3.10 (s, 3H), 1.40 (d, 3H, J=7 Hz).

(2S)-2-(4-{[4-(Trifluoromethyl)-1,3-oxazol-2-yl]amino}phenyl) propanamide (22)

Following the same procedure described for 13 and starting from (2S)-2-(4-{[4-(trifluoromethyl)-1,3-oxazol-2-yl]amino}phenyl)propanoic acid (19) (0.2 g, 0.67 mmol), after workup compound 22 (0.195 g, 0.65 mmol) was isolated as yellow oil (97%).

m.p 119°-121° C.; [α]$_D$=+36 (c=1; EtOAc); $^1$H-NMR (DMSO-d$_6$): δ 10.45 (bs, 1H, NH), 8.35 (s, 1H), 7.45 (d, 2H, J=7 Hz); 7.25 (d, 2H, J=7 Hz); 6.80 (bs, 2H, CONH$_2$); 3.50 (m, 1H); 1.25 (d, 3H, J=7 Hz).

(2S)-2-(4-{Methyl-[4-(trifluoromethyl)-1,3-oxazol-2-yl]amino}phenyl)propanamide (23)

Following the same procedure described for 13 and starting from (2S)-2-(4-{methyl[4-(trifluoromethyl)-1,3-oxazol-2-yl]amino}phenyl)propanoic acid (20) (0.065 g, 0.21 mmol), after workup, pure compound 23 (0.062 g, 0.20 mmol) was isolated as yellow oil (95%).

[α]$_D$=+18 (c=0.64; CH$_2$Cl$_2$); $^1$H-NMR (DMSO-d$_6$): δ 8.35 (s, 1H), 7.45 (d, 2H, J=7 Hz); 7.25 (d, 2H, J=7 Hz); 6.80 (bs, 2H, CONH$_2$); 3.50 (m, 1H); 3.40 (s, 3H); 1.25 (d, 3H, J=7 Hz).

(2S)-2-{[(2S)-2-(4-{[4-(Trifluoromethyl)-1,3-oxazol-2-yl]amino}phenyl)propanoyl]amino}propanoic acid (24)

Following the same procedure described for 16 and starting from (2S)-2-(4-{[4-(trifluoromethyl)-1,3-oxazol-2-yl]amino}phenyl)propanoic acid (19) (0.118 g, 0.39 mmol) and L-alanine methyl ester hydrochloride (0.035 g, 0.39 mmol), after workup and methyl ester hydrolysis, pure compound 24 (0.112 g, 0.29 mmol) was isolated as pale yellow oil (75%).

$^1$H-NMR (CDCl$_3$): δ 9.60 (bs, 1H, NH); 7.70 (s, 1H), 7.45 (m, 4H), 6.00 (bs, 1H, CONH), 4.60 (m, 1H); 3.70 (m, 1H); 1.60 (d, 3H, J=7 Hz) 1.35 (d, 3H, J=7 Hz).

(2S)—N-[(1S)-2-Amino-1-methyl-2-oxoethyl]-2-(4-{[4-(trifluoromethyl)-1,3-oxazol-2-yl]amino}phenyl) propanamide (25)

Following the same procedure described for 13 and starting from (2S)-2-{[(2S)-2-(4-{[4-(trifluoromethyl)-1,3-oxazol-2-yl]amino}phenyl)propanoyl]amino}propanoic acid (24) (0.1 g, 0.27 mmol) after workup pure compound 25 (0.103 g, 0.28 mmol) was isolated as transparent oil (93%).

$^1$H-NMR (CDCl$_3$): δ 9.60 (bs, 1H, NH); 7.70 (s, 1H), 7.45 (m, 4H), 6.00 (bs, 1H, CONH), 5.25 (bs, 2H, CONH$_2$) 4.60 (m, 1H); 3.70 (m, 1H); 1.60 (d, 3H, J=7 Hz), 1.35 (d, 3H, J=7 Hz).

TABLE 1

Biological activity of the preferred compounds

| Name | Structure | CXCL8 (% inhibition at $10^{-9}$ M) | CXCL1 (% inhibition at $10^{-8}$ M) |
|---|---|---|---|
| 2-(4-{[4-(trifluoromethyl)-1,3-thiazol-2-yl]amino}phenyl)propanoic acid (1) | 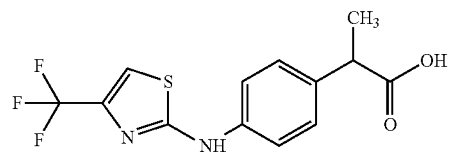 [SMILES: CC(C(=O)O)c1ccc(Nc2nc(C(F)(F)F)cs2)cc1] | 43 ± 7* | 40 ± 6 |
| 2-methyl-2-(4-{[4-(trifluoromethyl)-1,3-thiazol-2-yl]amino}phenyl)propanoic acid (2) | 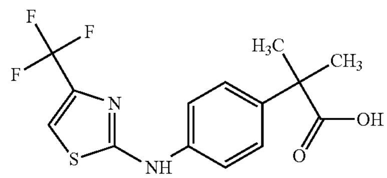 [SMILES: CC(C)(C(=O)O)c1ccc(Nc2nc(C(F)(F)F)cs2)cc1] | 56 ± 10 | 42 ± 9 |
| (2S)-2-(4-{[4-(trifluoromethyl)-1,3-thiazol-2-yl]amino}phenyl)propanoic acid (3) | 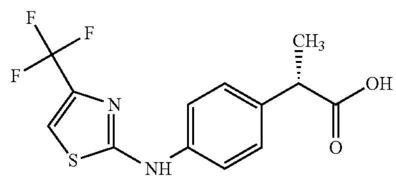 [SMILES: C[C@H](C(=O)O)c1ccc(Nc2nc(C(F)(F)F)cs2)cc1] | 66 ± 11 | 58 ± 6 |
| (2S)-2-(4-{[4-(trifluoromethyl)-1,3-thiazol-2-yl]amino}phenyl)propanoic acid sodium salt (3a) | 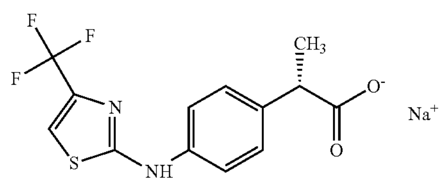 [SMILES: C[C@H](C(=O)[O-])c1ccc(Nc2nc(C(F)(F)F)cs2)cc1 ; [Na+]] | 64 ± 9 | 55 ± 8 |
| 2-{4-[(4-methyl-1,3-thiazol-2-yl)amino]phenyl}propanoic acid (4) | 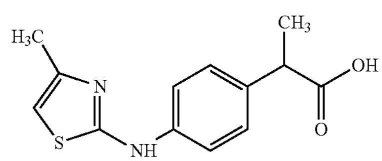 [SMILES: Cc1csc(Nc2ccc(C(C)C(=O)O)cc2)n1] | 46 ± 6* | 45 ± 10 |
| (2S)-2-{4-[(4-methyl-1,3-thiazol-2-yl)amino]phenyl}propanoic acid (5) | 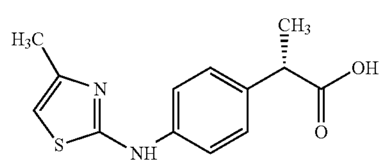 | 40 ± 11 | 38 ± 10 |
| 2-{4-[(4-tert-butyl-1,3-thiazol-2-yl)amino]phenyl}propanoic acid (6) | 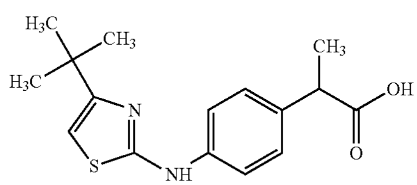 | 55 ± 10* | 36 ± 10 |
| (2S)-2-{4-[(4-tert-butyl-1,3-thiazol-2-yl)amino]phenyl}propanoic acid (7) | 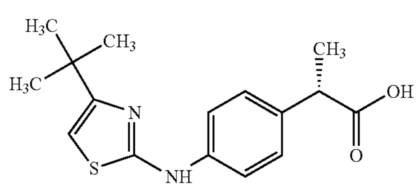 [SMILES: CC(C(=O)O)c1ccc(Nc2nc(C(C)(C)C)cs2)cc1] | 50 ± 8 | 45 ± 10 |

TABLE 1-continued

Biological activity of the preferred compounds

| Name | Structure | CXCL8 (% inhibition at $10^{-9}$ M) | CXCL1 (% inhibition at $10^{-8}$ M) |
| --- | --- | --- | --- |
| 2-(4-{methyl[4-(trifluoromethyl)-1,3-thiazol-2-yl]amino}phenyl)propanoic acid (8) | 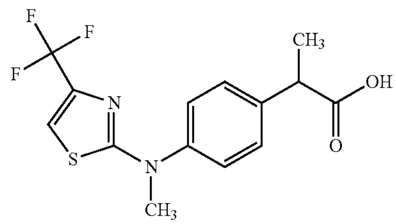 [SMILES: CC(C(=O)O)c1ccc(N(C)c2nc(C(F)(F)F)cs2)cc1] | 45 ± 5* | 39 ± 10 |
| (2S)-2-(4-{methyl[4-(trifluoromethyl)-1,3-thiazol-2-yl]amino}phenyl)propanoic acid (9) | 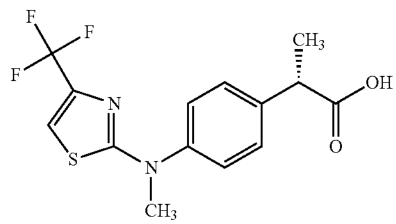 | 41 ± 7 | 40 ± 12 |
| (2S)-N-hydroxy-2-(4-{[4-(trifluoromethyl)-1,3-thiazol-2-yl]amino}phenyl) propanamide (10) | 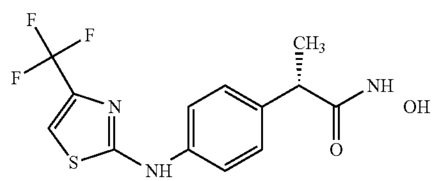 | 51 ± 10 | 47 ± 12 |
| (2S)-N-(methylsulfonyl)-2-(4-{[4-(trifluoromethyl)-1,3-thiazol-2-yl]amino}phenyl)propanamide (11) | 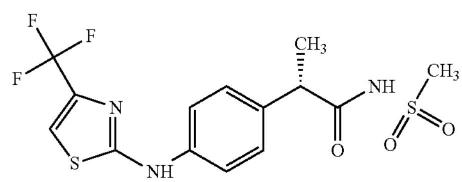 | 54 ± 16 | 39 ± 7 |
| (2S)-N-[(trifluoromethyl)sulfonyl]-2-(4-{[4-(trifluoromethyl)-1,3-thiazol-2-yl]amino}phenyl) propanamide (12) | 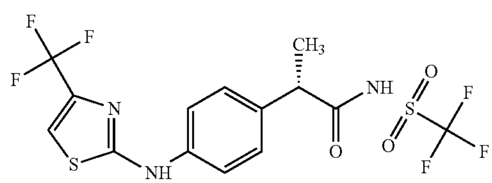 | 48 ± 13* | 30 ± 7 |
| (2S)-2-(4-{[4-(trifluoromethyl)-1,3-thiazol-2-yl]amino}phenyl propanamide (13) | 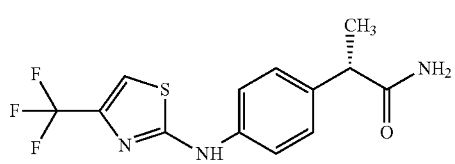 [SMILES: C[C@H](C(N)=O)c1ccc(Nc2nc(C(F)(F)F)cs2)cc1] | 47 ± 3 | 44 ± 9 |
| (2S)-2-(4-{methyl[4-(trifluoromethyl)-1,3-thiazol-2-yl]amino}phenyl)propanamide (14) | 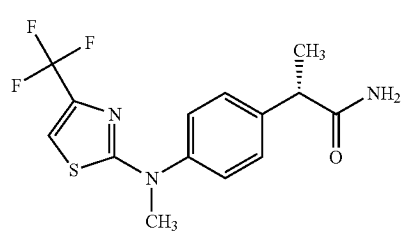 [SMILES: C[C@H](C(N)=O)c1ccc(N(C)c2nc(C(F)(F)F)cs2)cc1] | 45 ± 14 | 34 ± 13 |

TABLE 1-continued

Biological activity of the preferred compounds

| Name | Structure | CXCL8 (% inhibition at $10^{-9}$ M) | CXCL1 (% inhibition at $10^{-8}$ M) |
|---|---|---|---|
| (2S)-2-{4-[(4-tert.butyl-1,3-thiazol-2-yl)amino]phenyl}propanamide (15) | 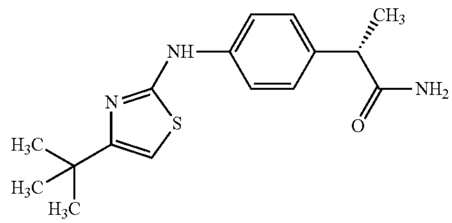 [SMILES: C[C@H](C(N)=O)c1ccc(Nc2nc(C(C)(C)C)cs2)cc1] | 48 ± 8 | 45 ± 10 |
| (2R)-2-{[(2S)-2-(4-{[4-(trifluoromethyl)-1,3-thiazol-2-yl]amino}phenyl)propanoyl]amino}propanoic acid (16) | 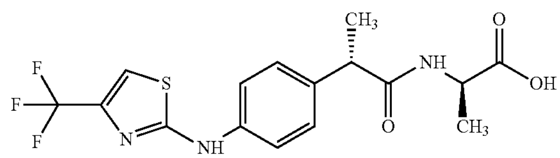 [SMILES: C[C@H](C(=O)N[C@H](C)C(=O)O)c1ccc(Nc2nc(C(F)(F)F)cs2)cc1] | 42 ± 7 | 30 ± 15 |
| (2S)-3-methyl-2-{[(2S)-2-(4-{[4-(trifluoromethyl)-1,3-thiazol-2-yl]amino}phenyl)propanoyl]amino}butanoic acid (17) | 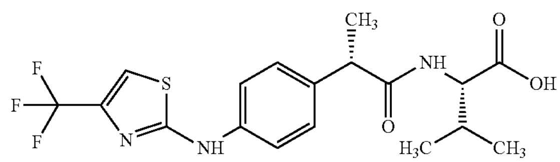 [SMILES: CC(C)[C@H](NC(=O)[C@@H](C)c1ccc(Nc2nc(C(F)(F)F)cs2)cc1)C(=O)O] | 39 ± 2 | 40 ± 12 |
| 2-{4-[(4-trifluoromethyl)-oxazol-2-yl]amino}phenyl propionic (18) | 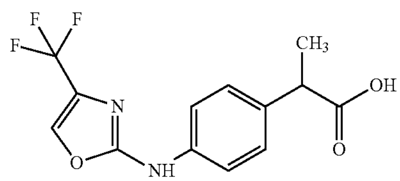 [SMILES: CC(C(=O)O)c1ccc(Nc2nc(C(F)(F)F)co2)cc1] | 47 ± 12* | 60 ± 9 |
| (2S)-2-(4-{[4-(trifluoromethyl)-1,3-oxazol-2-yl]amino} phenyl)propanoic acid (19) | 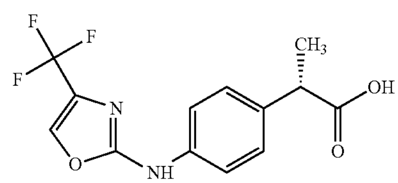 | 44 ± 10 | 36 ± 11 |
| (2S)-2-(4-{methyl[4-(trifluoromethyl)-1,3-oxazol-2-yl]amino} phenyl)propanoic acid (20) | 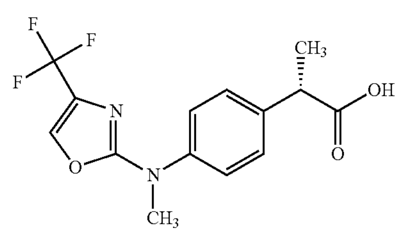 [SMILES: C[C@H](C(=O)O)c1ccc(N(C)c2nc(C(F)(F)F)co2)cc1] | 47 ± 8 | 44 ± 7 |
| (2S)-N-(methylsulfonyl)-2-(4-{[4-(trifluoromethyl)-1,3-oxazol-2-yl]amino}phenyl) propanamide (21) | 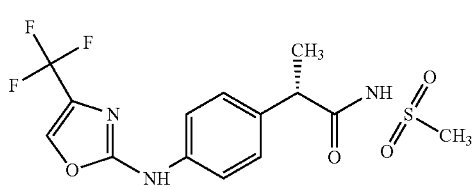 | 43 ± 6 | 37 ± 2 |
| (2S)-2-(4-{[4-(trifluoromethyl)-1,3-oxazol-2-yl]amino}phenyl)propanamide (22) | 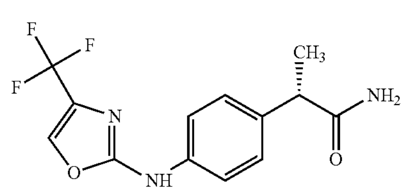 [SMILES: C[C@H](C(N)=O)c1ccc(Nc2nc(C(F)(F)F)co2)cc1] | 58 ± 5 | 49 ± 6 |

TABLE 1-continued

Biological activity of the preferred compounds

| Name | Structure | CXCL8 (% inhibition at $10^{-9}$ M) | CXCL1 (% inhibition at $10^{-8}$ M) |
|---|---|---|---|
| (2S)-2-(4-{methyl-[4-(trifluoromethyl)-1,3-oxazol-2-yl]amino}phenyl) propanamide (23) | 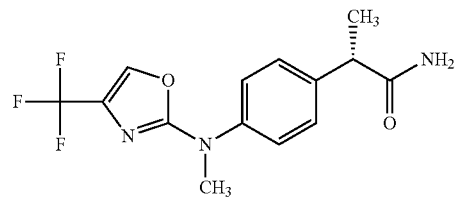 [SMILES: C[C@H](C(N)=O)c1ccc(N(C)c2nc(C(F)(F)F)co2)cc1] | 45 ± 13 | 39 ± 2 |
| (2S)-2-{[(2S)-2-(4-{[4-(trifluoromethyl)-1,3-oxazol-2-yl]amino}phenyl)propanoyl]amino}propanoic acid (24) | 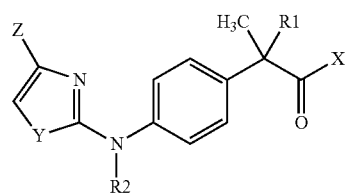 | 54 ± 12* | 34 ± 8 |
| (2S)-N-[(1S)-2-amino-1-methyl-2-oxoethyl]-2-(4-{[4-(trifluoromethyl)-1,3-oxazol-2-yl]amino}phenyl)propanamide (25) | 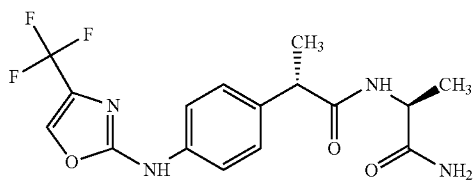 [SMILES: C[C@H](NC(=O)[C@@H](C)c1ccc(Nc2nc(C(F)(F)F)co2)cc1)C(N)=O] | 46 ± 12 | 39 ± 14 |

*tested at $10^{-8}$ M

The invention claimed is:

1. A compound of formula (I), (I)

wherein:
- $R_1$ is selected from:
  - H and $CH_3$;
- $R_2$ is selected from:
  - H and linear $C_1$-$C_4$-alkyl;
- X is OH or a residue of formula $NHR_3$:
  wherein:
  - $R_3$ is selected from:
    - H, OH, $C_1$-$C_5$-alkyl, $C_3$-$C_6$-cycloalkyl, $C_2$-$C_5$-alkenyl, $C_1$-$C_5$-alkoxy;
    - straight or branched $C_1$-$C_6$-alkyl, $C_3$-$C_6$-cycloalkyl, $C_2$-$C_6$-alkenyl, $C_1$-$C_6$-phenylalkyl, each of which is substituted with a carboxy (COOH) group; and
    - a residue of formula $SO_2R_4$ wherein $R_4$ is $C_1$-$C_2$-alkyl, $C_3$-$C_6$-cycloalkyl, $C_1$-$C_3$-haloalkyl;
- Y is a heteroatom selected from:
  - S, O and N;
- Z is a residue selected from:
  - halogen, $C_2$-$C_4$-alkenyl, $C_2$-$C_4$-alkynyl, $C_1$-$C_4$-alkoxy, hydroxy, carboxyl, $C_1$-$C_4$-acyloxy, phenoxy, cyano, nitro, amino, $C_1$-$C_4$-acylamino, halo-$C_1$-$C_3$-alkyl, halo-$C_1$-$C_3$-alkoxy, benzoyl, linear or branched $C_1$-$C_8$-alkanesulfonate, linear or branched $C_1$-$C_8$-alkanesulfonamides, and linear or branched $C_1$-$C_8$ alkyl sulfonylmethyl;

or a pharmaceutically acceptable salt thereof.

2. The compound according to claim 1 wherein the carbon atom bound to the phenyl ring is in RS configuration.

3. The compound according to claim 1,
wherein
- $R_1$ is $CH_3$;
- $R_2$ is selected from
  - H and $CH_3$;
- X is OH;
- Y is selected from
  - S and O;
- Z is selected from
  - halogen, $C_2$-$C_4$-alkenyl, $C_1$-$C_4$-acyloxy, phenoxy, cyano, nitro, halo-$C_1$-$C_3$-alkyl, benzoyl, linear or branched $C_1$-$C_8$-alkanesulfonate, and linear or branched $C_1$-$C_8$-alkanesulfonamides.

4. The compound according to claim 1 selected from:
- 2-[4-(4-trifluoromethylthiazol-2-yl)aminophenyl]propionic acid;
- 2-methyl-2-(4-{[4-(trifluoromethyl)-1,3-thiazol-2-yl]amino}phenyl)propanoic acid;
- (2S)-2-(4-{[4-(trifluoromethyl)-1,3-thiazol-2-yl]amino}phenyl)propanoic acid;
- (2S)-2-(4-{[4-(trifluoromethyl)-1,3-thiazol-2-yl]amino}phenyl)propanoic acid sodium salt;
- 2-(4-{methyl[4-(trifluoromethyl)-1,3-thiazol-2-yl]amino}phenyl)propanoic acid;
- (2S)-2-(4-{methyl[4-(trifluoromethyl)-1,3-thiazol-2-yl]amino}phenyl)propanoic acid;

(2S)—N-hydroxy-2-(4-{[4-(trifluoromethyl)-1,3-oxazol-2-yl]amino}phenyl) propanamide;

(2S)—N-(methylsulfonyl)-2-(4-{[4-(trifluoromethyl)-1,3-thiazol-2-yl]amino}phenyl)propanamide;

(2S)—N-[(trifluoromethyl)sulfonyl]-2-(4-{[4-(trifluoromethyl)-1,3-thiazol-2-yl]amino}phenyl) propanamide;

(2S)-2-(4-{[4-(trifluoromethyl)-1,3-thiazol-2-yl]amino}phenyl propanamide;

(2S)-2-(4-{methyl[4-(trifluoromethyl)-1,3-thiazol-2-yl]amino}phenyl) propanamide;

(2S)-2-{[(2S)-2-(4-{[4-(trifluoromethyl)-1,3-thiazol-2-yl]amino}phenyl) propanoyl]amino}propanoic acid;

(2S)-3-methyl-2-{[(2S)-2-(4-{[4-(trifluoromethyl)-1,3-thiazol-2-yl]amino}phenyl)propanoyl]amino}butanoic acid;

2-{4-[(4-trifluoromethyl)-oxazol-2-yl]amino}phenyl propionic;

(2R)-2-(4-{[4-(trifluoromethyl)-1,3-oxazol-2-yl]amino}phenyl)propanoic acid;

(2S)-2-(4-{methyl[4-(trifluoromethyl)-1,3-oxazol-2-yl]amino}phenyl)propanoic acid;

(2S)—N-(methylsulfonyl)-2-(4-{[4-(trifluoromethyl)-1,3-oxazol-2-yl]amino}phenyl)propanamide;

(2S)-2-(4-{[4-(trifluoromethyl)-1,3-oxazol-2-yl]amino}phenyl)propanamide;

(2S)-2-(4-{methyl-[4-(trifluoromethyl)-1,3-oxazol-2-yl]amino}phenyl)propanamide; and (2S)-2-{[(2S)-2-(4-{[4-(trifluoromethyl)-1,3-oxazol-2-yl]amino}phenyl) propanoyl]amino}propanoic acid.

5. The compound according to claim 1 which is (2S)-2-(4-{[4-(trifluoromethyl)-1,3-thiazol-2-yl]amino}phenyl)propanoic acid.

6. A pharmaceutical composition comprising a compound according to claim 1 in admixture with a suitable carrier thereof.

7. A method for inhibiting CXCL8 induced human PMNs chemotaxis comprising administering to a subject a pharmaceutically effective amount of a compound according to claim 1.

8. A method for treating transient cerebral ischemia, damages caused by ischemia and reperfusion, bullous pemphigo, rheumatoid arthritis, idiopathic fibrosis or glomerulonephritis comprising administering to a subject in need thereof a pharmaceutically effective amount of a compound according to claim 1.

9. A process for the preparation of the compound of claim 1 comprising the steps of: converting (R,S) or (S) methyl 2-[4-(carbamothioylamino)phenyl]propanoate or (R,S) or (S) methyl 2-[4-carbamoylamino]phenyl]propanoate into the related 4-heterocycle derivative; subsequently hydrolyzing the compound obtained in the previous step to the carboxylic acid of formula (I) wherein X is OH, and reacting this carboxylic acid with sulfonamides or amines, thereby affording the compound of formula (I) when X is NHR$_3$.

10. The compound according to claim 1 wherein Z is —CF$_3$.

11. A compound of formula:

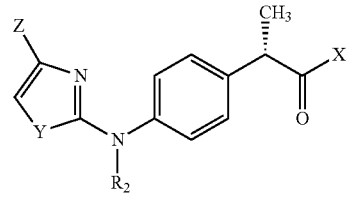

wherein
R$_2$ is selected from
H and linear C$_1$-C$_4$-alkyl;
X is OH or a residue of formula NHR$_3$
wherein
R$_3$ is selected from
H, OH, C$_1$-C$_5$-alkyl, C$_3$-C$_6$-cycloalkyl, C$_2$-C$_5$-alkenyl, C$_1$-C$_5$-alkoxy;
straight or branched C$_1$-C$_6$-alkyl, C$_3$-C$_6$-cycloalkyl, C$_2$-C$_6$-alkenyl, C$_1$-C$_6$-phenylalkyl, each of which is substituted with a carboxy (COOH) group; and
a residue of formula SO$_2$R$_4$ wherein R$_4$ is C$_1$-C$_2$-alkyl, C$_3$-C$_6$-cycloalkyl, C$_1$-C$_3$-haloalkyl;
Y is a heteroatom selected from:
S, O and N;
Z is a residue selected from:
halogen, C$_2$-C$_4$-alkenyl, C$_2$-C$_4$-alkynyl, C$_1$-C$_4$-alkoxy, hydroxy, carboxyl, C$_1$-C$_4$-acyloxy, phenoxy, cyano, nitro, amino, C$_1$-C$_4$-acylamino, halo-C$_1$-C$_3$-alkyl, halo-C$_1$-C$_3$-alkoxy, benzoyl, linear or branched C$_1$-C$_8$-alkanesulfonate, linear or branched C$_1$-C$_8$-alkanesulfonamides, and linear or branched C$_1$-C$_8$ alkyl sulfonylmethyl;
or a pharmaceutically acceptable salt thereof.

12. A compound, the compound being:
(2S)—N-[(1S)-2-amino-1-methyl-2-oxoethyl]-2-(4-{[4-(trifluoromethyl)-1,3-oxazol-2-yl]amino}phenyl)propanamide.

* * * * *